US005621073A

United States Patent [19]
Dickhardt et al.

[11] Patent Number: 5,621,073
[45] Date of Patent: Apr. 15, 1997

[54] CHROMATOGRAPHIC PROCESS FOR PURIFICATION OF INSULIN

[75] Inventors: Rainer Dickhardt; Bernhard Unger, both of Kelkheim; Claudia Gräfe, Königstein/Tanus, all of Germany

[73] Assignee: Hoechst Aktiengesellschaft, Frankfurt am Main, Germany

[21] Appl. No.: 430,273

[22] Filed: Apr. 28, 1995

Related U.S. Application Data

[63] Continuation of Ser. No. 991,261, Dec. 16, 1992, abandoned.

[30] Foreign Application Priority Data

Dec. 18, 1991 [DE] Germany .......................... 41 41 794.1
Jun. 20, 1992 [DE] Germany .......................... 42 20 293.0

[51] Int. Cl.$^6$ .................................................. A61K 38/28
[52] U.S. Cl. ...................... 530/305; 530/303; 530/304; 530/412; 514/3
[58] Field of Search .................................. 530/305, 412; 514/3

[56] References Cited

U.S. PATENT DOCUMENTS

| | | |
|---|---|---|
| 4,129,560 | 12/1978 | Zoltobrocki . |
| 4,601,852 | 7/1986 | Obermeier et al. . |
| 5,008,241 | 4/1991 | Markussen .................................. 514/3 |
| 5,245,008 | 9/1993 | Dickhardt et al. ....................... 530/309 |

FOREIGN PATENT DOCUMENTS

44412/89B  5/1990  Australia .

0368187A2  5/1990  European Pat. Off. .
0474213A1  3/1992  European Pat. Off. .

OTHER PUBLICATIONS

European Search Report, EP 92 12 1255, May 24, 1994.
B.S. Welinder et al., "Separation, Isolation and Characterization of the Four Monoiodinated Insulin Tracers Using Reversed–Phase High–Performance Liquid Chromatography," Journal of Chromatography, 265 (1983) pp. 301–309.
E.P. Kroeff et al., "Production Scale Purification of Biosynthetic Human Insulin by Reversed–Phase High–Performance Liquid Chromatography," Journal of Chromatography, 461 (1989) pp. 45–61.
W.S. Hancock et al., "Biochemical Applications of Preparative Liquid Chromatography," in Preparative Liquid Chromatography, ed. by B.A. Bidlingmeyer, Journal of Chromatography LIbrary, vol. 38, pp. 203–233.
Jean River et al., Journal of Chromatography, vol. 268: 112–119 (1983).
"Reverse–phase high–performance liquid chromatography of insulin Resolution and recovery in relation to column geometry and buffer components", Benny S. Welinder et al., Journal of Chromatography, 361:357–367 (1986).

*Primary Examiner*—David Lukton
*Attorney, Agent, or Firm*—Finnegan, Henderson, Farabow, Garrett & Dunner, L.L.P.

[57]  ABSTRACT

A process is described for obtaining insulin, which is virtually free from proteases and/or insulin acetylated at position A9, by chromatography in aqueous, buffered solvents which contain water-miscible organic solvents, on lipophilically modified silica gel, wherein the dissolving buffer contains acetone or acetonitrile.

11 Claims, No Drawings

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Gly  Ile  Val  Glu  Gln  Cys  Cys  Thr  Ser  Ile  Cys  Ser  Leu  Tyr  Gln  Leu
 1                  5                        10                       15

Glu  Asn  Tyr  Cys
                20
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

```
Phe  Val  Asn  Gln  His  Leu  Cys  Gly  Ser  His  Leu  Val  Glu  Ala  Leu  Tyr
 1                  5                        10                       15
```

| Leu | Val | Cys | Gly | Glu | Arg | Gly | Phe | Phe | Tyr | Thr | Pro | Lys |
|-----|-----|-----|-----|-----|-----|-----|-----|-----|-----|-----|-----|-----|
|     |     |     | 20  |     |     |     |     | 25  |     |     |     |     |

CHROMATOGRAPHIC PROCESS FOR PURIFICATION OF INSULIN

This application is a continuation of application Ser. No. 07/991,261, filed Dec. 16, 1992, now abandoned.

BACKGROUND OF THE INVENTION

The purification of insulins or insulin derivatives on lipophilically modified (reversed phase) silica gels is known from analytic separation procedures and has been used successfully for many years in high pressure liquid chromatography (HPLC) (W S Welinder et al., J. Chrom., 361, (1986) 357–367). On an analytical scale protein quantities in the μg region are added to a column of steel, glass or plastic that is filled with modified silica gel, and subsequently eluted with a mixed fluid stream (mainly acidic, aqueous buffer solutions with a constant or variable concentration of organic solvents). In a separation of this type the protein loading is substantially less than 30 μg/ml of column volume.

The insulins from previous chemical conversions, for example from strongly acidic ester cleavages or enzymatic (trans)peptidation processes and from crystallization purifications, usually contain concomitant substances with similar properties. They can be purified by ion exchange chromatography by the choice of particular pH values, if adequate electric charge differences exist (U.S. Pat. No. 4,129,560). The disadvantage of this method lies in the dilution effect, and the consequent loss of valuable material in the supernatants during the working up of the precipitates, in the relatively long cycle time and in the fact that the total recovery and thus the yield is less.

Insulin preparations with depot properties frequently contain protamines which extend the length of action of insulins. Protamines are arginine-rich proteins which are obtained from roe. Quality tests on depot insulin preparations regularly showed an inexplicable loss of the depot properties after the preparation had been stored for some time. Such insulin preparations are completely unsuitable for the patient, since their use can readily lead to insulin overdosing, which may sometimes lead to the death of the patient following hypoglycemic shock.

Precise investigations of these insulin preparations showed that the loss of the depot properties is caused by a slow degradation of the protamines by traces of proteases. Additionally, it was found that the major quantity of proteases in these preparations arises from the enzymatic transpeptidation of porcine insulin to human insulin ester/ether or from proteolytic processes for the cleavage of insulin-like precursors. Although a large part of the proteases, for example trypsin, is separated off by the commonly-employed chromatographic procedures, it is evident that residual quantities of proteases do remain in the insulin preparations and lead there to the loss of depot properties.

In the preparation of insulin by genetic engineering the serine situated at position A9 of the insulin is also acetylated by the microorganism as a by-product, so that an insulin derivative is formed that is acetylated at the serine hydroxyl group. This insulin derivative has thus far only been observed in the preparation of insulin with *Escherichia coli* using genetic engineering. The complete separation of this acetylated insulin derivative from human insulin has so far only been achieved at the cost of a low yield of human insulin, when the process described in the European Patent Application with the Publication No. 0 474 213 is used. Additionally, it is evident that in this process separation can no longer be achieved if the concentration of acetylated insulin exceeds 5%. Furthermore, it is not possible using this process to obtain insulin that is virtually protease free.

DESCRIPTION OF THE PREFERRED EMBODIMENTS

A process has now been found for obtaining insulin, which is virtually free from proteases and/or insulin acetylated at position A9, by chromatography in aqueous, buffered eluents which contain water-miscible organic solvents, on lipophilically modified silica gel, wherein 1A) the mixture of proteases and/or insulin acetylated at position A9 and insulin is dissolved in a buffer, 1B) the elution is carried out with a buffered eluent which contains zwitterions and optionally has been adjusted to a pH in the vicinity of the isoelectric point of the insulin to be purified, the insulin fractions obtained are concentrated as required and subsequently the insulin fractions obtained 2A) are dissolved in a dissolving buffer which contains acetone or acetonitrile, 2B) the solution obtained is added to the column, 2C) the column is washed with the dissolving buffer and 2D) the insulin to be purified is eluted with a buffered eluent which contains zwitterions and optionally has been adjusted to a pH in the vicinity of the isoelectric point of the insulin to be purified.

Surprisingly, the presence of acetone or acetonitrile in the dissolving buffer at step 2A of the process effects a markedly improved separation of the proteases and of the insulins acetylated at position A9 from insulin, so that the problems that have been described with insulin formulations containing protamines no longer arise.

The mixtures to be purifed composed of proteases and/or insulin acetylated at position A9 and insulin can arise from a large number of enzymatic processes, for example proteolytic elimination of pre- and/or pro-sequences of preproinsulins, elimination of C- or N-terminal amino acids of insulin or transamidations of porcine insulin to human insulin or human insulin derivatives. Additionally, the insulin acetylated at position A9 that is contained in the mixtures to be purified can arise from a large number of insulin constructs expressed by means of genetic engineering.

The proteases that can be separated off in the process are for example trypsin, lysylendopeptidase, carboxypeptidase A, clostripain or achromobacter protease. Trypsin is preferred.

In the present application the following compounds are understood by the term insulin. Insulins which are of animal or human origin, e.g. human insulin or porcine insulin, insulin precursors, e.g. proinsulins or preproinsulins, or recombinant insulins or insulin derivatives that are expressed from genetically modified microorganisms. Additionally, insulin derivatives can also be used that for example were prepared by chemical or enzymatic derivatization, e.g. des-Phe-B1-insulin, insulin-β-ketenesulfonate, diargininein-sulin (B31, B32), monoarginineinsulin, diphenylalanineinsulin (B31, B32) (U.S. Pat. No. 4,601,852), or $Gly^{A21}$-$Arg^{B31}$-$Arg^{B32}$-human insulin (EP 368 187).

In the process according to the invention insulins of the formula I are preferably employed

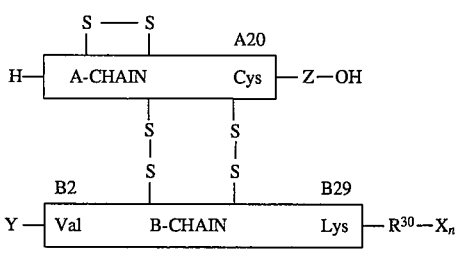

(I)

in which

R$^{30}$ is the residue of a genetically encodable L-amino acid,

X is a hydroxyl group, a physiologically acceptable organic group of basic character with up to 50 carbon atoms, a genetically encodable L-amino acid whose terminal carboxyl function, if present, can exist free, as an ester function, as an amide function, as a lactone or reduced to CH$_2$OH, n is an integer from 0 to 10, Y is hydrogen or L-phenylalanine, and Z is a genetically encodable L-amino acid, and the A and B chains have the sequences of animal or human insulin.

Preferably used insulins have the formula I, in which

R$^{30}$ is L-alanine or L-threonine and

X is one or more L-amino acids from the group comprising L-arginine, L-lysine or L-phenylalanine and Z is L-glycine, L-alanine, L-serine, L-threonine, L-aspartic acid or L-glutamic acid, and A1 to A20 or B2 to B29 is the amino acid sequence of human insulin, porcine insulin or bovine insulin.

The amino acid sequence A1 to A20 of human insulin is:

(SEQ ID NO: 1)

Gly Ile Val Glu Gln Cys Cys Thr Ser Ile Cys Ser
Leu Tyr Gln Leu Glu Asn Tyr Cys

The amino acid sequence B1 to B29 of human insulin is:

(SEQ ID NO: 2)

Phe Val Asn Gln His Leu Cys Gly Ser His Leu
Val Glu Ala Leu Tyr Leu Val Cys Gly Glu Arg
Gly Phe Phe Tyr Thr Pro Lys

Additionally, it was found that steps 2A to 2D of the abovementioned chromatographic process are exceptionally suitable on their own, without steps 1A and 1B, for obtaining insulin from insulin mixtures containing insulin, insulin acetylated at position A9 and proteases, as well as insulin mixtures containing insulin and insulin acetylated at position A9.

The insulins which are acetylated at position A9 and which can be separated off in the process according to the invention are for example human insulin acetylated at position A9 or A9-acetylated insulin of the formula I, where R$^{30}$, X, n, Y and Z have the abovementioned definitions.

Preferably, insulin derivatives of the formula I are separated from insulins of the formula I that are acetylated at position A9. In particular a separation of A9-acetylated human insulin from human insulin is effected.

Insulin and insulin derivatives can be used both in relatively impure condition as well as in pre-purified form (e.g. by gel chromatography). Following repeated crystallization and also following gel chromatography, insulin is still contaminated with insulin-like concomitant substances with a very similar molecular weight, which, at suitably chosen pH, differ in charge from each other and from insulin, but form complexes with insulin (U.S. Pat. No. 4,129,560). Examples of such substances are deamidoinsulins, arginineinsulin and diarginineinsulin and insulin ethyl ester.

By lipophilically modified silica gel is understood a silica gel to which a hydrophobic matrix has been applied. Examples of a hydrophobic matrix are alkanes with a chain length of from 3 to 20 carbon atoms, in particular 8 to 18 carbon atoms. Additionally, the particle size can vary within a wide range, for example from 5 to 60 μm, in particular from 10 to 50 μm. The pore width can also vary within a wide range; favorable pore widths are from 50 to 300 Å, in particular 100 to 200 Å. Examples of lipophilically modified silica gel materials are:

®Nucleosil, Macherey & Nagel GmbH +Co.KG, D üren, Germany spherical and non-spherical materials of various particle size up to 45 μm, 100 Å pore width, C8- or C18-modified.

®LiChroprep, E. Merck Co., Darmstadt, Germany non-spherical and spherical materials of various particle sizes up to 40 μm, 60–250 Å pore width, C8- or C18-modified;

®LiChrospher Select B, E. Merck Co., Darmstadt, Germany spherical material up to 25 μm particle size, C8-modified;

®Waters Prep, Millipore GmbH, Eschborn, Germany C18-modified, 50–105 μm non-spherical, 100 Å pore width;

®Zorbax Pro10, DuPont de Nemours (Germany) GmbH, Bad Homburg, Germany C8-modified, 10 μm, spherical, 100 Å pore width;

®Kromasil, EKA Nobel Co., Nobel Industries, Sweden C4-, C8- and C18-modified, up to 20 μm, spherical, 100, 150 or 200 Å pore width.

Zwitterions are compounds which can pick up and also lose protons, i.e. form cations in acid solution and anions in alkaline solution, such as for example α-amino acids, betaine or betaine derivatives. Preferred zwitterions are glycine, glutamine or betaine (N-trimethyl-glycine). Glycine is particularly preferred.

The isoelectric point (IEP) of an insulin or an insulin derivative is that pH at which the total of the cationic charges and anionic charges of the dissolved insulin is equal to zero. For example, the IEP of porcine insulin lies in the region of pH 5.3 to 5.4. By the term "in the vicinity of the electric point" is understood in particular pH values that lie within about 1 pH unit above or below the IEP of the insulin to be purified. Particularly preferred are pH values which lie up to 0.5 pH units above or below the IEP.

By the term "virtually protease-free insulin" are understood mixtures of insulins and proteases in which the protease activity is 0 to 4 mAU/min, preferably 0.01 to 1 mAU/min, in particular 0.02 to 0.08 mAU/min.

The protease activity is determined by measuring the kinetics of the elimination of a chromophore (4-nitroanilide) from the substrate carbobenzoxy-Val-Gly-Arg-4-nitroanilide acetate (Chromozym-Try; Order No. 378488 Boehringer Mannheim). The elimination reaction is measured spectrophotometrically over a time period of 60 min at a wavelength of 405 nm. Under these circumstances the increase in the measured absorption is directly proportional to the tryptic activity in the product. The unit of slope of the absorption line is milliabsorption units per minute (mAU/min.).

By the term "insulin which is virtually free from insulin acetylated at position A9" are understood insulin preparations which have a content of A9-acetylated insulin which is less than 0.5%, preferably less than 0.2%, in particular less than 0.1%.

The eluents contain a buffer substance which keeps the pH of the eluent constant. Suitable buffer substances are known in the literature, for example phosphates, salts of alkali metals or alkaline earth metals such as sodium citrate or potassium acetate, ammonium citrate, ammonium acetate, ammonium sulfate or ammonium chloride. Additionally, the eluents contain organic solvents which are miscible with water, such as for example alcohols, ketones, methyl acetate, dioxane or acetonitrile.

Alcohols such as n- or iso-propanol, methanol, ethanol or methyl acetate are preferred.

For the first chromatography step (process steps 1A and 1B) the concentration of the water-miscible organic solvents is 1 to 70%, preferably 10 to 50%, particularly preferably 10 to 35%. The concentration of the buffer substance is about 1 mmol/l to 140 mmol/l, based on water as the solvent, preferably 2 mmol/l to 120 mmol/l. The concentration of the zwitterions can vary within a wide range. Advantageous quantities are 1 mmol/l to 140 mmol/l, based on water as the solvent, preferably 10 mmol/l to 110 mmol/l.

The temperature during the chromatography is 0° C. to 50° C., preferably 15° to 30° C., particularly preferably 15° to 20° C. The operating pressure during the chromatography is substantially constant. The chromatography can be carried out under various pressures, e.g. the chromatography can be carried out under a pressure of from 5 to 400 bar, in particular 20 to 100 bar.

The loading of the columns, and chromatography and elution of the insulins and insulin derivatives is achieved according to known, conventional, technical methods. The loading of the column with the insulin solution to be purified is achieved preferably with aqueous-alcoholic or purely aqueous buffer solution. The insulin solution has a protein content of from about 1 to 10%, preferably 3%.

The elution of the insulins is achieved by the process according to the invention at a constant concentration of the buffer substances (isocratically) or by changing the proportion of water-miscible organic solvent in the buffer. The change in the proportion of organic solvent takes place in such a way that the concentration of the organic solvent used increases as a function of the elution volume, specifically preferably as a linear function.

The concentration of the insulin from the eluates following chromatography takes place by precipitation with zinc or by crystallization. In this context, the solution can beforehand, as required, be substantially freed of solvent by means of vacuum distillation or its concentration can be reduced by dilution with water. In any case, the concentration of solvent before the precipitation or crystallization should be 10% or less, in order to keep the protein content in the supernatant at <50 mg/l. The insulin precipitates which arise can be isolated by decanting, centrifugation or filtration, and dried.

For the second chromatography step (process steps 2A to 2B) the concentration of the water-miscible organic solvents is 1 to 90%, preferably 10 to 60%, particularly preferably 10 to 35%. The concentration of the buffer substance is about 1 mmol/l to 2 mol/l, based on water as the solvent, preferably 25 mmol/l to 1 mol/l. The concentration of the zwitterions can vary within a wide range. Advantageous quantities are 10 mmol/l to 1 mol/l, based on water as the solvent, preferably 20 mmol/l to 500 mmol/l.

The temperature during the chromatography is 0° C. to 50° C., preferably 15° to 30° C., particularly preferably 15° to 20° C. The operating pressure during the chromatography is substantially constant. The chromatography can be carried out under various pressures, e.g. the chromatography can be carried out under a pressure of from 5 to 400 bar, in particular 20 to 100 bar.

The loading of the columns, chromatography and elution of the insulins and insulin derivatives is achieved according to known, conventional, technical methods. The loading of the columns with the insulins to be purified and/or insulin derivatives takes place with a dissolving buffer which contains acetone or acetonitrile. Suitable buffer substances are known in the literature, for example phosphates, salts of alkali metals or alkaline earth metals such as sodium citrate or potassium acetate, ammonium citrate, ammonium acetate, ammonium sulfate or ammonium chloride. Additionally zwitterions can also be present in the dissolving buffer. The concentration of acetone or acetonitrile can vary within wide limits. Acetone or acetonitrile quantities of 5 percent by volume to 50 percent by volume have proved to be favorable. Acetonitrile or acetone concentrations of 10 to 40 percent by volume are preferred, in particular of 25 to 35 percent by volume.

The pH of the dissolving buffer is about pH 1 to 6, preferably pH 2 to 5, in particular pH 3 to 4.

The columns are washed from once to five times with the dissolving buffer, preferably once to three times, in particular once. The insulin solution has a protein content of from 1 to 10%, preferably 3%.

With the process according to the invention elution of the insulins takes place at a constant concentration of the buffer substances and a constant concentration (isocratically) of the water-miscible organic solvents, or by changing the proportion in the buffer of the water-miscible organic solvents. The change in the proportion of the organic solvents is achieved in such a manner that the concentration of the organic solvent being used increases as a function of the elution volume, specifically preferably as a linear function.

The separation of the insulin from the eluates following chromatography takes place by precipitation with zinc or by crystallization. In this context, the solution can beforehand, as required, be substantially freed of solvent by means of vacuum distillation or its concentration can be reduced by dilution with water. In any case, the concentration of solvent before the precipitation or crystallization should be 10% or below, so that the protein content in the supernatant is kept to less than 50 mg/l. The precipitates of pure insulin that arise can be isolated by decanting, centrifugation or filtration, and dried.

The process according to the invention is suitable not only for analytical chromatography, but also for preparative chromatography, particularly when the process according to the invention is carried out with preparative HPLC equipment.

By the term "preparative chromatography" is understood a purification process with the aim not just of analyzing but of obtaining pure products. The amount of pure products can vary within wide limits, for example from 1 mg to 50 kg, preferably from 50 mg to 15 kg.

In the following examples, Examples 1, 6 and 7 are processes according to applicants' invention and Examples 2, 3, 4 and 5 are comparative processes. Percentages refer to weight, unless otherwise indicated.

EXAMPLE 1

Buffer A: 0.1M ammonium sulfate, 0.1M glycine, 0.025M sodium acetate, pH 5.5, 5% propanol Buffer B: 0.1M ammonium sulfate, 0.1M glycine, 0.025M sodium acetate, pH 5.5, water/n-propanol in the proportion 1:1

Sorbent ®Kromasil C8, 13 μm, 100 Å pore width

Column dimensions: 2 cm×25 cm.

The column is loaded with a solution of 0.5 g of crude human insulin, prepared by genetic engineering and containing 2.5% of acetylated human insulin, in 25 ml of a dissolving buffer which contains 0.1M glycine, 0.1M NaCl, 32% by vol. acetone, pH 3.5.

After the loading of the human insulin solution onto the column it is washed with one column volume of the dissolving buffer.

With a flow rate of 9 ml/min and an increase in the propanol concentration from 14% to 25%, the individual protein components are eluted separately within 90 min. Following crystallization or precipitation and drying, human insulin is obtained as the main fraction at a purity of more than 98% and with a yield of 86.2%, based on the insulin employed.

Determination of the concentration of A9-acetylated human insulin is carried out as follows:

For the analysis, HPLC columns (4 mm×250 mm) from Machery & Nagel Co., Düren, filled with ®Nucleosil C18, 120 Å, 5 μm are employed.

Buffer A: 35 mM sodium phosphate 300 mM sodium chloride 25% acetonitrile 75% water pH 3.0

Buffer B: 35 mM sodium phosphate 50 mM sodium chloride 65% acetonitrile 35% water pH 3.0

At a column temperature of 40° C., a flow rate of 1 ml/min and a gradient of 12% buffer B to 21% buffer B within 25 min, the acetylated derivative is eluted from the column with a retention time difference of 6 min after the human insulin peak. Using this analytical method the insulin derivative can be very satisfactorily separated from human insulin, identified and quantified.

After the purification the content of A9-acetylated human insulin is less than 0.1%.

EXAMPLE 2

In the following comparative experiment the chromatography takes place as in Example 1, except that the dissolving buffer only contains 0.1M glycine/HCl, pH 2.8. Yield: 58% with a purity of more than 98%. The content of A9-acetylated human insulin is 0.2%.

EXAMPLE 3

Buffer A: 0.15M ammonium sulfate, 0.15M glycine, 0.025M sodium acetate, pH 5.5, 5% n-propanol;

Buffer B: 0.15M ammonium sulfate, 0.15M glycine, 0.025M sodium acetate, pH 5.5, water/n-propanol in the ratio 1:1.

Sorbent: Kromasil C8, 13 μm, 100 Å pore width, from EKA Nobel.

Column dimensions: 6 cm×25 cm.

The column is loaded with a solution of 10 g of reaction mixture from the transamidation of porcine insulin with trypsin, dissolved in 200 ml of 0.1M glycine/HCl buffer, pH 2.8. The trypsin activity is more than 10,000mAU/min. With a flow rate of 40 ml/min and an increase in the propanol concentration from 14 to 30% the individual protein components are eluted separately within 120 minutes. Following crystallization or precipitation and drying, human insulin-B30 di-tert-butyl threonine ester/ether is obtained as the main fraction with a purity of >97% and with a yield of 93%, based on the insulin employed.

The determination of protease activity is carried out as follows:

In this test the kinetics are determined of the elimination of a chromophore (4-nitroanilide) from the substrate carbobenzoxy-Val-Gly-Arg-4-nitroanilide acetate (Chromozym-Try; Order No. 378488 Boehringer Mannheim). The progress of the elimination reaction is measured spectrophotometrically over a time period of 60 min. at a wavelength of 405 nm. Under these circumstances the increase in the measured absorption is directly proportional to the tryptic activity in the product. The slope of the absorption line is determined (unit: milliabsorption units per minute (mAU/min.)) and is a direct measure of the protease content.

The test is carried out as follows:

7.5 mg of human insulin are dissolved in one milliliter of dissolving buffer, with stirring, within 30 min.

Dissolving buffer: 200 mM TRIS pH 8.0 1 mM EDTA

The Chromozym substrate is dissolved in water at a concentration of 1 mg/ml.

The reaction is started at 37° C. by addition of 200 μl of substrate solution to 1 ml of sample solution and then immediately measured spectrophotometrically at 405 nm. The absorption of the reaction solution at this wavelength is recorded continuously for 60 minutes. To ascertain the tryptic activity, the slope of the absorption line is determined.

A tryptic activity of 250 mAU/min is measured.

EXAMPLE 4

The chromatography takes place as described in Example 3, except that the conditions were changed as follows:

0.1M glycine 0.05M ammonium sulfate

Column dimensions: 6 cm×25 cm

A tryptic activity of 5 to 10 mAU/min is measured.

EXAMPLE 5

The chromatography takes place as described in Example 4, except that the column dimensions are 30 cm×30 cm.

A tryptic activity of 20 to 25 mAU/min is measured.

EXAMPLE 6

Buffer A: 0.05M ammonium sulfate, 0.1M glycine, 0.025M sodium acetate, pH 5.5, 5% propanol;

Buffer B: 0.05M ammonium sulfate, 0.1M glycine, 0.025M sodium acetate, pH 5.5, water/n-propanol in the ratio 1:1.

Sorbent: Kromasil C8, 13 μm, 100 Å pore width, from EKA Nobel.

Column dimensions: 6 cm×25 cm.

A solution of 10 g of reaction mixture from the trifluoroacetic acid cleavage of human insulin-B30 di-tert-butyl threonine ester/ether with a protein content of 79% is purified on a column as described in Example 4. Subsequently, precipitation takes place as in Example 3 in order to concentrate the insulin-containing fractions, and the precipitate is subsequently dissolved in a mixture of 200 ml of 0.1M glycine, 0.1M NaCl, 32 percent by volume acetone, pH 3.5, and this solution is loaded onto the column. After the human insulin solution has been loaded onto the column it is washed with one column volume of the dissolving buffer. Subsequently elution takes place within 45 minutes by means of a gradient of 17% buffer B to 19% B. All other conditions are analogous to Example 4.

The tryptic activity is less than 0.05 mAU/min.

EXAMPLE 7

The chromatography takes place as in Example 6. The column dimensions are 30 cm×30 cm. The tryptic activity is less than 0.05 mAU/min.

| Sequence protocol |
|---|
| SEQ ID NO: 1<br>Sequence type: amino acid (AA)<br>Sequence length: 20 AA |

| Gly 1 | Ile | Val | Glu | Gln 5 | Cys | Cys | Thr | Ser | Ile 10 | Cys | Ser | Leu |
|---|---|---|---|---|---|---|---|---|---|---|---|---|
| Tyr | Gln 15 | Leu | Glu | Asn | Tyr | Cys 20 | | | | | | |

| SEQ ID NO: 2<br>Sequence type: AA<br>Sequence length: 29 AA |
|---|

| Phe 1 | Val | Asn | Gln | His 5 | Leu | Cys | Gly | Ser | His 10 | Leu | Val | Glu |
|---|---|---|---|---|---|---|---|---|---|---|---|---|
| Ala | Leu 15 | Tyr | Leu | Val | Cys | Gly 20 | Glu | Arg | Gly | Phe 25 | Phe | Tyr |
| Thr | Pro | Lys | | | | | | | | | | |

We claim:

1. A process for obtaining insulin which is virtually free from both trypsin and insulin acetylated at position A9, wherein said insulin is of formula I,

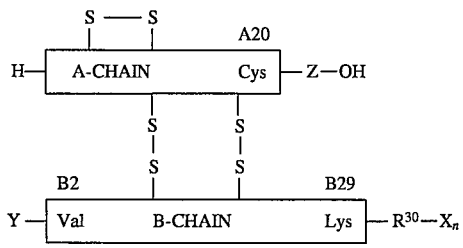

(I)

in which $R^{30}$ is the residue of a genetically encodable L-amino acid,

X is a hydroxyl group, a genetically encodable L-amino acid whose terminal carboxyl group, if present, can exist free, as an ester function, as an amide function, as a lactone, or reduced to $CH_2OH$, n is an integer from 0 to 10, Y is hydrogen or L-phenylalanine Z is a genetically encodable L-amino acid, and the A and B chains have the sequences of animal or human insulin, said process comprising:

1A) dissolving a mixture of insulin and trypsin or a mixture of insulin and insulin acetylated at position A9 in a buffer;

1B) eluting the product of step 1A with a buffered eluent comprising zwitterions selected from amino acids or betaine;

1C) concentrating the insulin fractions obtained in step 1B;

2A) dissolving the insulin fractions obtained in step 1C in a dissolving buffer comprising acetone or acetonitrile;

2B) adding the solution obtained in step 2A to a column comprising a lipophilically modified silica gel;

2C) washing the column with the dissolving buffer; and 2D) eluting the product of step 2C with a buffered eluent comprising zwitterions selected from amino acids or betaine.

2. The process of claim 1, wherein said zwitterions are α-amino acids.

3. The process as claimed in claim 1, wherein the dissolving buffer comprises 5 to 50 percent by volume of acetone.

4. The process as claimed in claim 1, wherein the pH of the dissolving buffer is 2 to 5.

5. The process as claimed in claim 1, wherein an insulin derivative of the formula I is obtained, in which $R^{30}$ is L-alanine or L-threonine and X is L-arginine, L-lysine or L-phenylalanine, Z is L-glycine, L-alanine, L-serine, L-threonine, L-aspartic acid or L-glutamic acid and A1 to A20 or B2 to B29 is the amino acid sequence of human insulin, porcine insulin or bovine insulin.

6. The process as claimed in claim 1, wherein human insulin is obtained.

7. The process as claimed in claim 1, wherein preparative high pressure liquid chromatography equipment is employed.

8. The process as claimed in claim 1, wherein said buffered eluent used in step 1B is adjusted to a pH in the vicinity of the isoelectric point of the insulin to be purified prior to step 1B.

9. The process as claimed in claim 1, wherein said buffered eluent used in step 2D is adjusted to a pH in the vicinity of the isoelectric point of the insulin to be purified prior to step 2D.

10. The process as claimed in claim 1, wherein the dissolving buffer comprises 10 to 40 percent by volume of acetone.

11. The process as claimed in claim 1, wherein the pH of said dissolving buffer is 3 to 4.

* * * * *